United States Patent [19]

Helmus et al.

[11] Patent Number: 5,569,197
[45] Date of Patent: Oct. 29, 1996

[54] DRUG DELIVERY GUIDEWIRE

[75] Inventors: Michael N. Helmus, St. Louis Park; Michael R. Forman, St. Paul, both of Minn.

[73] Assignee: Schneider (USA) Inc, Plymouth, Minn.

[21] Appl. No.: 360,488

[22] Filed: Dec. 21, 1994

[51] Int. Cl.$^6$ ............................................. A61M 29/00
[52] U.S. Cl. .......................... 604/96; 604/53; 604/282
[58] Field of Search ........................ 604/53, 95, 96, 604/280, 281, 49, 282

[56] References Cited

U.S. PATENT DOCUMENTS

| | | | |
|---|---|---|---|
| 4,085,757 | 4/1978 | Pevsner | 128/325 |
| 4,213,461 | 7/1980 | Pevsner | 128/348 |
| 4,446,867 | 5/1984 | Leveen et al. | 128/344 |
| 4,509,523 | 4/1985 | Pevsner | 128/658 |
| 4,517,979 | 5/1985 | Pecenka | 128/325 |
| 4,545,367 | 10/1985 | Tucci | 128/1 R |
| 4,739,768 | 4/1988 | Engelson . | |
| 4,762,129 | 8/1988 | Bonzel | 128/344 |
| 4,773,899 | 9/1988 | Spears | 604/20 |
| 4,854,330 | 8/1989 | Evans, III et al. | 128/772 |
| 4,925,445 | 5/1990 | Sakamoto et al. | 604/95 |
| 4,946,466 | 8/1990 | Pinchuk et al. | 606/194 |
| 4,947,864 | 8/1990 | Shockey et al. | 128/772 |
| 4,953,553 | 9/1990 | Tremulis | 128/637 |
| 4,998,923 | 3/1991 | Samson et al. | 606/194 |
| 5,061,240 | 10/1991 | Cherian | 604/96 |
| 5,090,957 | 2/1992 | Moutafis et al. | 604/96 |
| 5,102,415 | 4/1992 | Guenther et al. | 606/159 |
| 5,163,906 | 11/1992 | Ahmadi | 604/101 |
| 5,176,674 | 1/1993 | Hofmann | 606/7 |
| 5,201,757 | 4/1993 | Heyn et al. | 606/198 |
| 5,209,729 | 5/1993 | Hofmann et al. | 604/96 |
| 5,226,889 | 7/1993 | Sheiban | 604/101 |
| 5,226,899 | 7/1993 | Lee et al. | 604/282 |
| 5,232,445 | 8/1993 | Bonzel | 604/96 |
| 5,238,004 | 8/1993 | Sahatjian et al. | 128/772 |
| 5,243,996 | 9/1993 | Hall | 128/772 |
| 5,256,144 | 10/1993 | Kraus et al. | 604/96 |
| 5,261,877 | 11/1993 | Fine et al. | 604/49 |
| 5,267,573 | 12/1993 | Evans et al. | 128/772 |
| 5,279,546 | 1/1994 | Mische et al. | 604/22 |
| 5,295,961 | 3/1994 | Niederhauser et al. | 604/96 |
| 5,306,247 | 4/1994 | Pfenninger | 604/96 |
| 5,322,508 | 6/1994 | Viera | 604/52 |
| 5,334,168 | 8/1994 | Hemmer | 604/281 |
| 5,336,205 | 8/1994 | Zenzen et al. | 604/53 X |
| 5,368,579 | 11/1994 | Sandridge | 604/53 X |

FOREIGN PATENT DOCUMENTS

| | | |
|---|---|---|
| 0491349A3 | 6/1992 | European Pat. Off. . |
| 3818279A1 | 12/1989 | Germany . |
| 92/07594 | 5/1992 | WIPO . |

OTHER PUBLICATIONS

"Fastracker™ The Frictionless System", Product literature, Target Therapeutics®, Dec. 1993.
"Tracker®–18 Infusion Catheter", Product literature, Target Therapeutics®, May 1991.
"Fastracker™–10", Product literature, Target therapeutics®, Jul. 1993.
"Fastracker™–18", Product literature, Target Therapeutics®, Jun. 1994.
"Pharmacologic Adjuncts to Percutaneous Transluminal Coronary Angioplasty", *Coronary Balloon Angioplasty*, 1994, pp. 231–260.
Schetsky, L. McDonald, "Shape Memory Alloys", *Encyclopedia of Chemical Technology*, Third Edition, John Wiley & Sons, 1982, vol. 20, pp. 726–736.

*Primary Examiner*—John D. Yasko
*Attorney, Agent, or Firm*—Peter C. Richardson; Lawrence C. Akers; Philip C. Strassburger

[57] ABSTRACT

This invention relates to a drug delivery device having a hollow tube which is configured to serve as a guide wire for intraluminal procedures. The distal portion of the tube has at least one opening which has a diameter suitable for the infusion of a drug formulation therethrough. The tube is preferably formed from a superelastic material such as nickel-titanium alloy. This invention also relates to various methods of using this drug delivery device in thrombolytic and other intraluminal procedures.

34 Claims, 6 Drawing Sheets

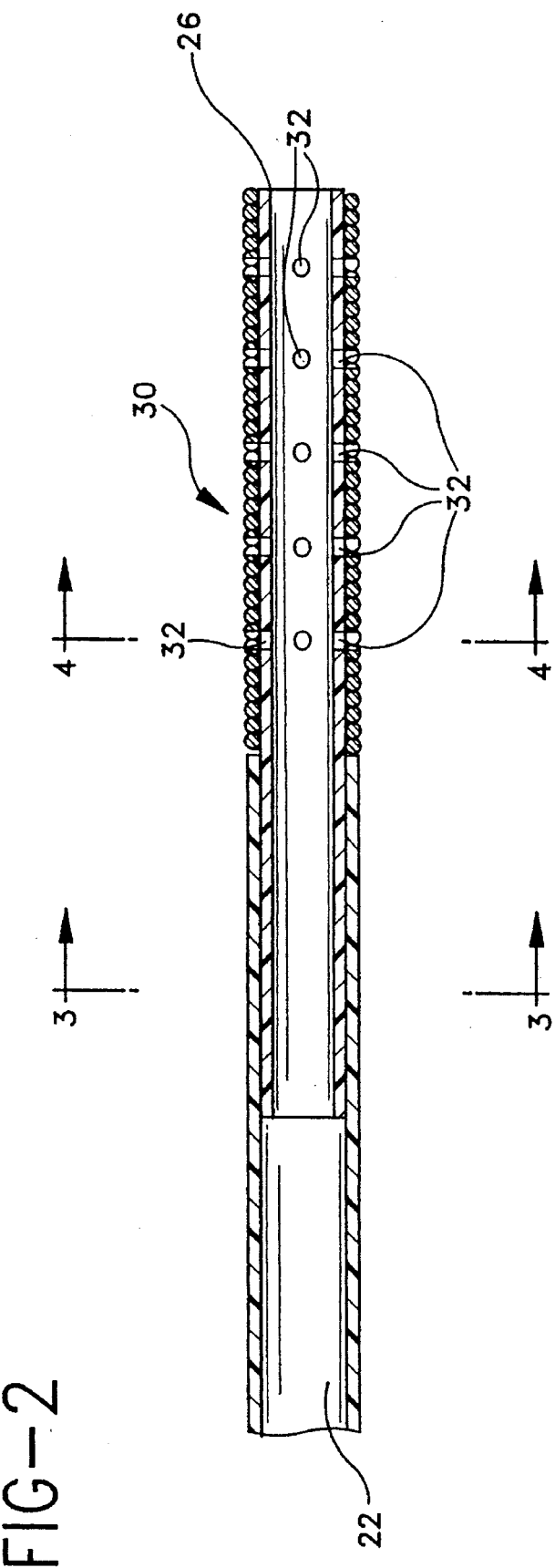
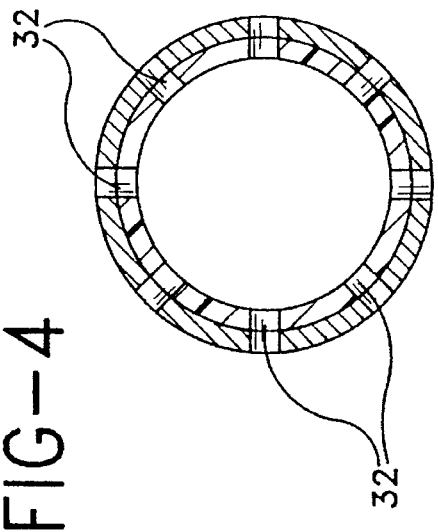
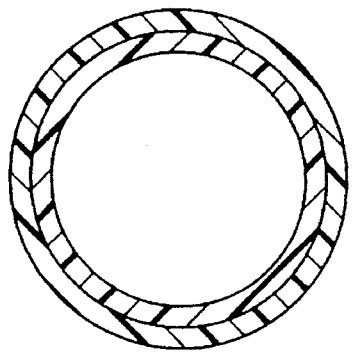

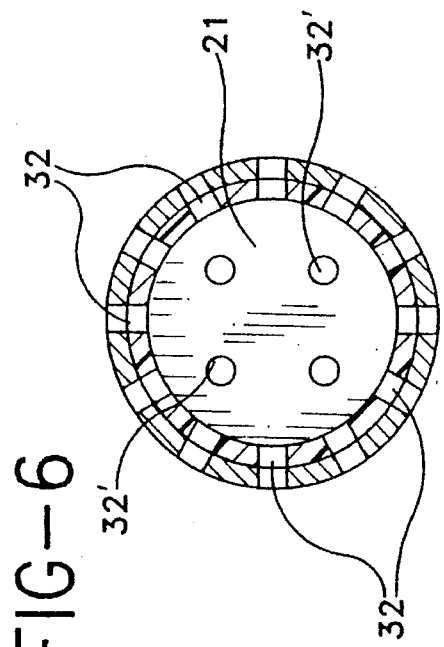
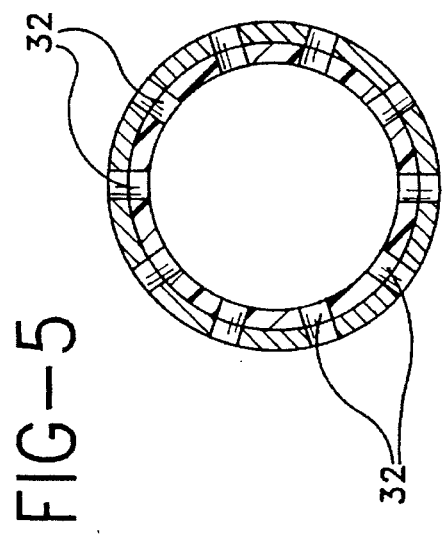
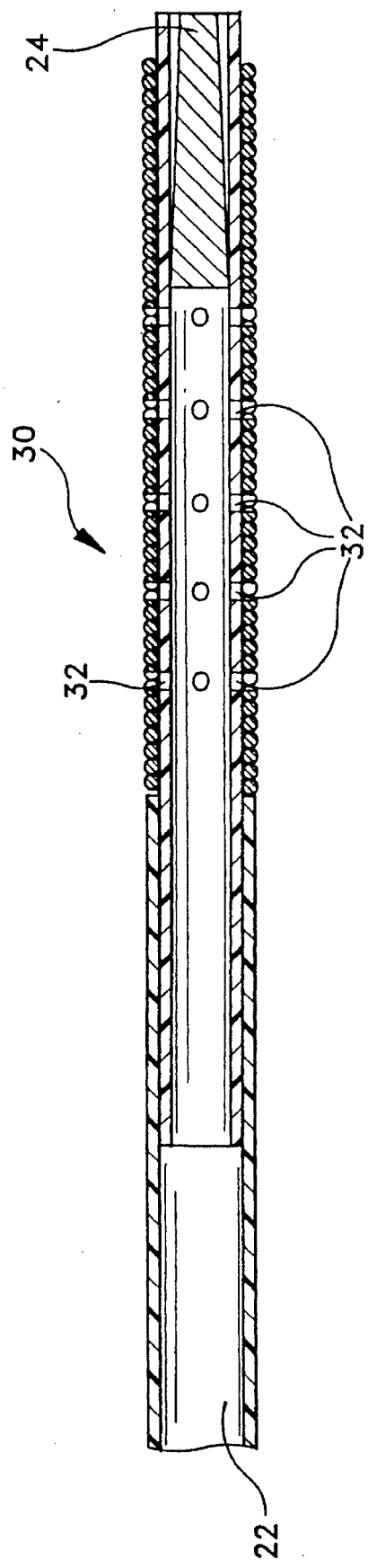

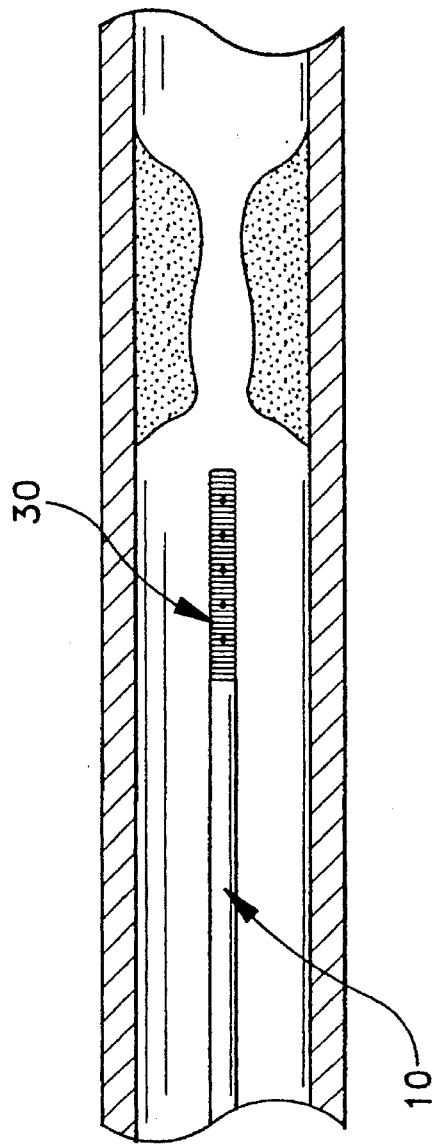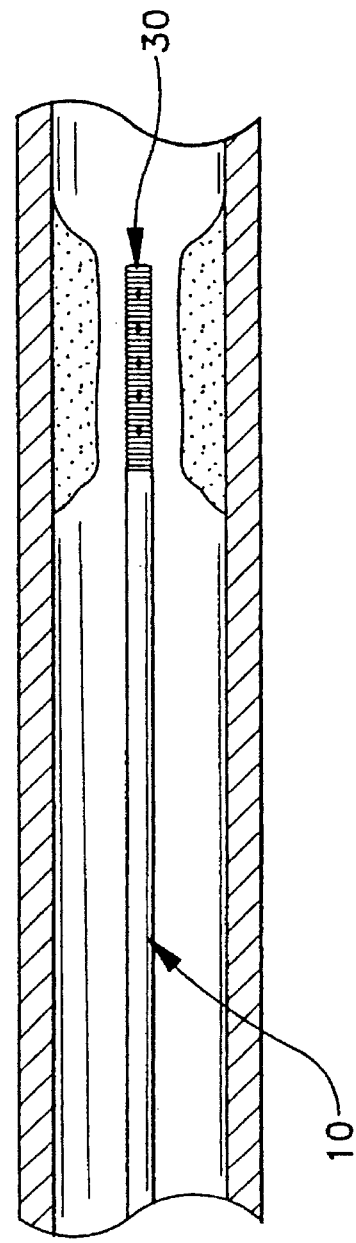

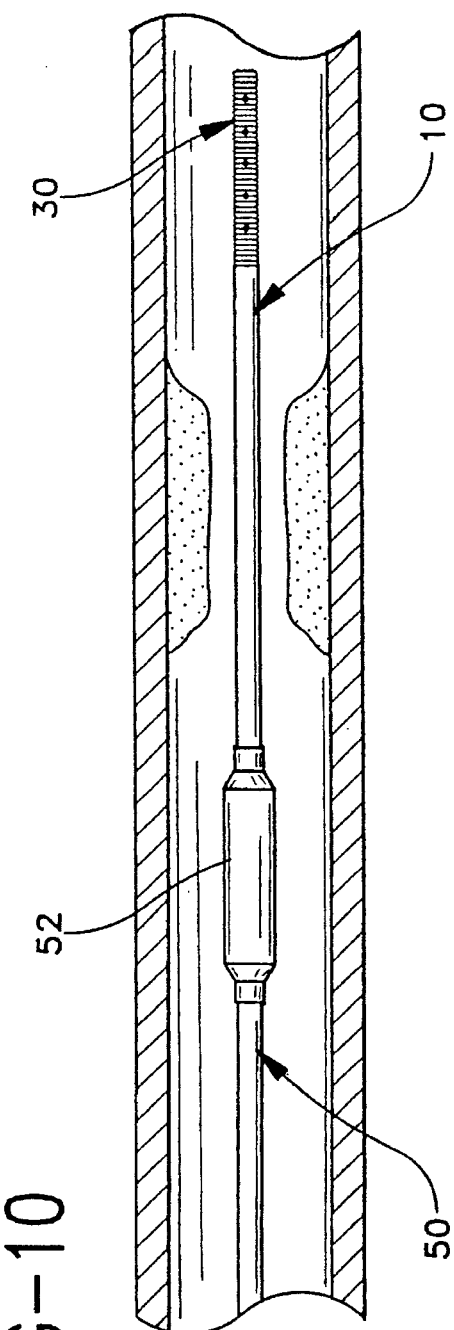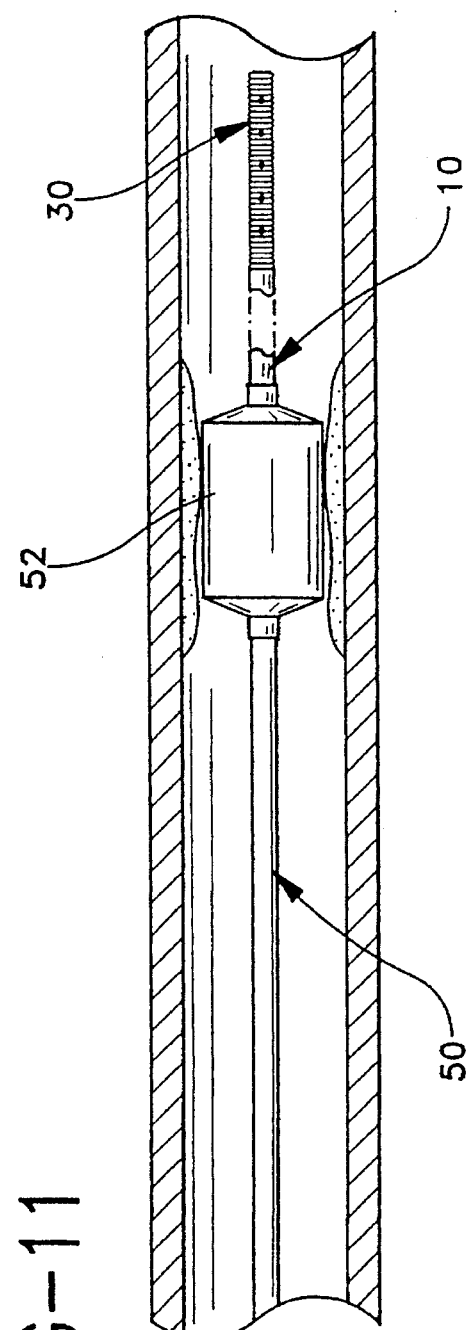

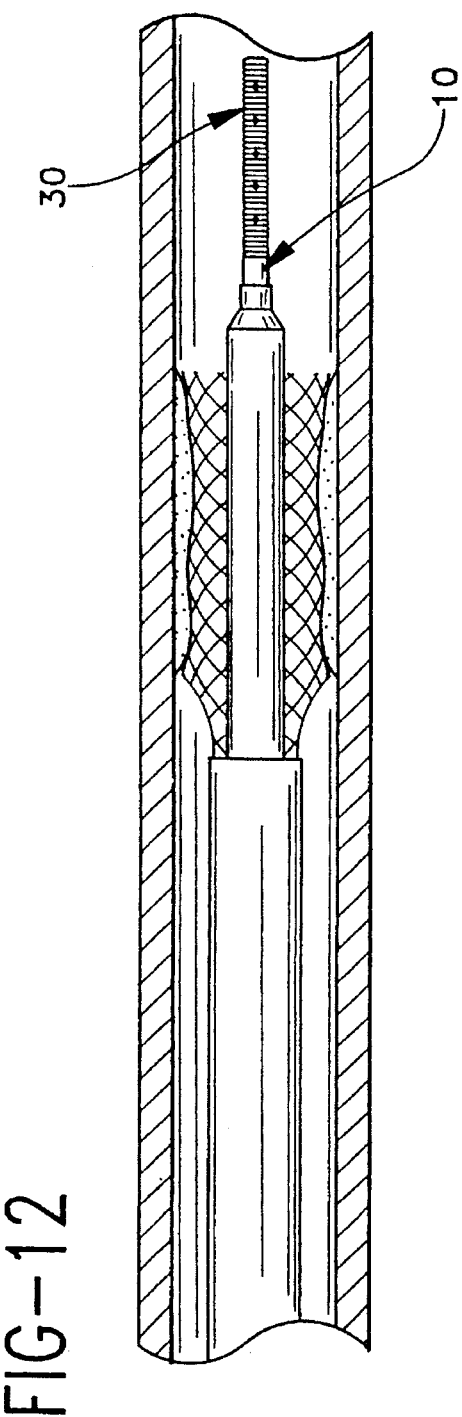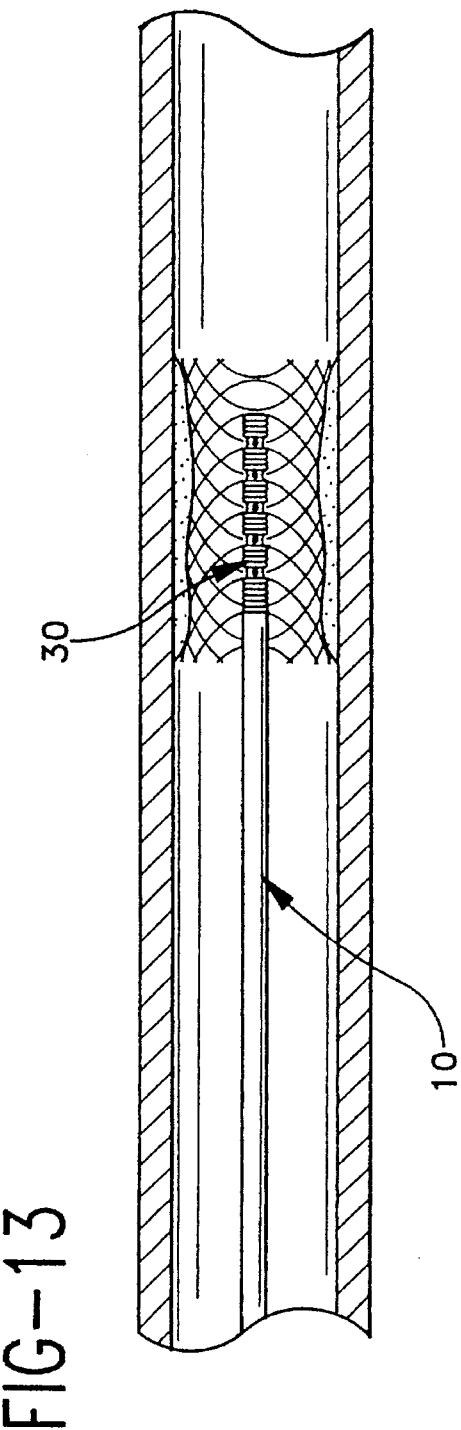

DRUG DELIVERY GUIDEWIRE

BACKGROUND OF THE INVENTION

The present invention relates to a drug delivery device in the form of a hollow guidewire with at least one perforation at the distal end thereof.

Balloon angioplasty is generally an effective method for treating vascular disease, especially atherosclerosis. The build up of plaque in the lumen of a blood vessel, i.e. a stenosis, narrows the lumen and could eventually occlude the lumen if left untreated. Such a situation in a coronary artery can cause a myocardial infarction, i.e., a heart attack. In balloon angioplasty, a balloon located on the distal end of a catheter is used to expand the blood vessel to restore its patency in the area of the stenotic lesion.

Such standard balloon angioplasty procedures, however, may not be suitable when a stenosis substantially occludes the lumen of the blood vessel. If the outer diameter of a deflated balloon dilatation catheter is larger than the void in a blood vessel, the balloon will be unable to cross the lesion to allow the balloon to inflate and restore patency to the blood vessel. A similar problem occurs when a stenosis is located in a very narrow blood vessel which is inaccessible to standard balloon dilatation catheters having outer diameters of about 0.032 to about 0.042 inches (0.081 cm to 0.107 cm) along its distal portion. Occlusions can be alleviated by performing a thrombolytic procedure. Such a procedure is described in "Pharmacologic Adjuncts to Percutaneous Transluminal Coronary Angioplasty," Coronary Balloon Angioplasty, 1994, at pages 231–260: 250,000 IU of urokinase is initially infused over 10 or 20 minutes for native coronary arteries and abrupt closure. For proximal occlusions, a guide-catheter can be used for infusion. An SOS wire or distal lumen of a standard balloon catheter is preferred for more distal occlusions. For distal occlusions with tenuous guidewire position, a Tracker-18 Infusion Catheter (Target Therapeutics, San Jose, Calif.) or a multiple side-hole infusion catheter may be used. Occasionally a further 250,000 IU of urokinase is administered if there is no evidence of any change. After positioning the infusion wire distally into the graft, 50,000 IU/hour of urokinase is infused through both the guide and the infusion catheter. Alternatively, if the guide position is stable, this can be used alone to infuse urokinase into the graft. PTCA of the underlying lesions can be attempted afterwards when thrombus is not visible or when sufficient clearing has occurred to allow flow into the distal native coronary artery.

In some cases, a thrombolytic procedure will only be partially successful, and a thrombus will remain. In other cases, a thrombotic obstruction will be removed revealing an underlying lesion. In such cases, it may be desirable to perform a balloon angioplasty procedure at the site of the remaining thrombus or the site of the underlying lesion.

After a thrombolytic procedure, a stent may be implanted to support the vessel wall. Such stents are used to enlarge and support the lumen, provide a smooth luminal surface, reinforce vessel dissections, tack-up tissue flaps, reduce the risk of plaque rupture, decrease the incidence of complications and reduce the incidence of restenosis. Many different types of stents may be used, such as radially self-expanding stents or balloon-expandable stents. Typically, the stent is placed on the distal end of a wire guided delivery catheter so the stent can be maneuvered adjacent to the treatment site and deployed there. After deployment it may be necessary to expand the stent further with a balloon catheter.

It is therefore an object of the invention to provide a drug delivery device that can cross a very tight occlusion or cross an extremely narrow blood vessel and dispense a drug at a desired site.

It is a further object of the invention to provide a drug delivery device that can be used to deliver a drug to a desired site and then act as a guide wire for an angioplasty balloon catheter, a stent delivery device or other devices for performing intraluminal procedures.

SUMMARY OF THE INVENTION

These and other objects are achieved by the drug delivery device of the present invention. This drug delivery device has a hollow tube and at least one perforation at the distal end of the tube in fluid communication therewith. It may have a flexible distal segment connected to the distal end of the hollow tube and/or a removable hub connected adjacent the proximal end of the hollow tube. The device should be both flexible and have sufficiently longitudinal rigidity. Flexibility is desirable in order for the device to navigate the sometimes tortuous path used to get to the treatment site. This is especially true where the treatment site is in a blood vessel, such as renal, carotid or coronary arteries. Longitudinal rigidity is preferred to provide "pushability." This "pushability" ensures that the physician will be able to push the device through the anatomy to the appropriate treatment site. Preferably the tube is made from a shape-memory or superelastic material. Such a material includes nickel-titanium alloys, nickel and its alloys and titanium and its alloys. This material allows the angioplasty device to be formed with an outer diameter as small as about 0.010 inches (0.025 cm) so it can function as a standard guide wire for a PTCA balloon dilatation catheter or a stent delivery catheter.

In sum, the present invention relates to a drug delivery device having a hollow tube configured to serve as a guidewire for intraluminal devices with a proximal portion and a distal portion and defining a lumen therein. The distal portion of the tube has at least one opening with a diameter suitable for the infusion of a drug formulation therethrough. The at least one opening is in fluid communication with the lumen. The hollow tube may be formed from a superelastic material, such as a material selected from the group consisting of a nickel-titanium alloy, nickel and its alloys, and titanium and its alloys. The tube may have an outer diameter of from about (0.010 inches 0.025 cm) to about 0.038 inches (0.097 cm), preferably about 0.014 inches (0.036 cm). The lumen may have a diameter of from about 0.005 inches (0.013 cm) to about 0.035 inches (0.089 cm). A flexible distal segment may be connected to the distal portion of the hollow tube, and it may be made of a generally solid core wire which may have a helical coil spring arranged coaxially about the generally solid core wire.

The present invention also relates to a drug delivery-dilatation device, with a hollow tube configured to serve as a guidewire for intraluminal devices and having a proximal portion and a distal portion and defining a lumen therein. The distal portion of the tube has at least one opening with a diameter suitable for the infusion of a drug formulation therethrough. The at least one opening is in fluid communication with the lumen. The device also has a balloon dilatation catheter with a dilatation balloon attached to a catheter and a guide wire lumen adapted to receive the hollow tube. The hollow tube may be formed from a superelastic material, such as a material selected from the group consisting of a nickel-titanium alloy, nickel and its alloys, and titanium and its alloys. The tube may have an outer diameter of from about 0.010 inches (0.025 cm) to about 0.038 inches (0.097 cm), preferably about 0.014 inches (0.036 cm). The lumen may have a diameter of from about 0.005 inches (0.013 cm) to about 0.035 inches (0.089 cm). The catheter guide wire lumen may be at least partially disposed about the hollow tube.

The present invention also relates to drug delivery-stent deployment device with a hollow tube configured to serve as a guidewire for intraluminal devices and having a proximal portion and a distal portion and defining a lumen therein. The distal portion of the tube has at least one opening with a diameter suitable for the infusion of a drug formulation therethrough. The at least one opening is in fluid communication with the lumen. The device also has a stent deployment catheter with a guide wire lumen adapted to receive the hollow tube. The hollow tube may be formed from a superelastic material, such as a material selected from the group consisting of a nickel-titanium alloy, nickel and its alloys, and titanium and its alloys. The tube may have an outer diameter of from about 0.010 inches (0.25 cm) to about 0.038 inches (0.097 cm), preferably about 0.014 inches (0.036 cm). The lumen may have a diameter of from about 0.005 inches (0.013 cm) to about 0.035 inches (0.089 cm). The catheter guide wire lumen may be at least partially disposed about the hollow tube.

The present invention also relates to a method for removing a thrombotic blockage using a drug delivery device with a hollow tube having a proximal portion and a distal portion and defining a lumen therein, wherein the distal portion has a drug delivery portion having at least one opening having a diameter suitable for the infusion of a thrombolytic agent therethrough, the opening being in fluid communication with the lumen. The method includes advancing the drug delivery device through a patient's vasculature so that the drug delivery portion is located at about a site of thrombotic obstruction, and infusing the thrombolytic agent through the opening to reduce the thrombotic obstruction. An underlying lesion may be revealed after the thrombolytic agents are infused. The method may also include advancing a balloon dilatation catheter over at least part of the hollow tube so that a dilatation balloon is located adjacent to the underlying lesion, and dilatating the underlying lesion with the dilatation balloon. The method may also include advancing a stent delivery catheter with a stent contained therein over at least part of the hollow tube, and deploying the stent from the stent delivery catheter. The method may also include withdrawing the stent delivery catheter, advancing a balloon catheter over at least part of the hollow tube until a balloon is located within the stent, and inflating the balloon to expand the stent.

BRIEF DESCRIPTION OF THE DRAWINGS

The following figures have been provided to illustrate, but not limit, the present invention.

FIG. 2 is a side elevational view in section of the distal portion of another embodiment of the drug delivery device of this invention;

FIG. 3 is a cross-sectional view taken along line 3—3 in FIG. 2;

FIG. 4 is a cross-sectional view taken along line 4—4 in FIG. 2;

FIG. 5 is a cross-sectional view of an alternative embodiment of the present invention;

FIG. 6 is a cross-sectional view of an alternative embodiment of the present invention;

FIG. 7 is a side elevational view in section of the distal portion of yet another embodiment of the drug delivery device of this invention;

FIGS. 8–11 are schematic views showing a method of using the drug delivery device of this invention in a PTCA procedure; and FIGS. 12–13 are schematic views showing a method of using the delivery device of this invention in a stent deployment procedure.

DETAILED DESCRIPTION OF THE INVENTION

Figure 1:
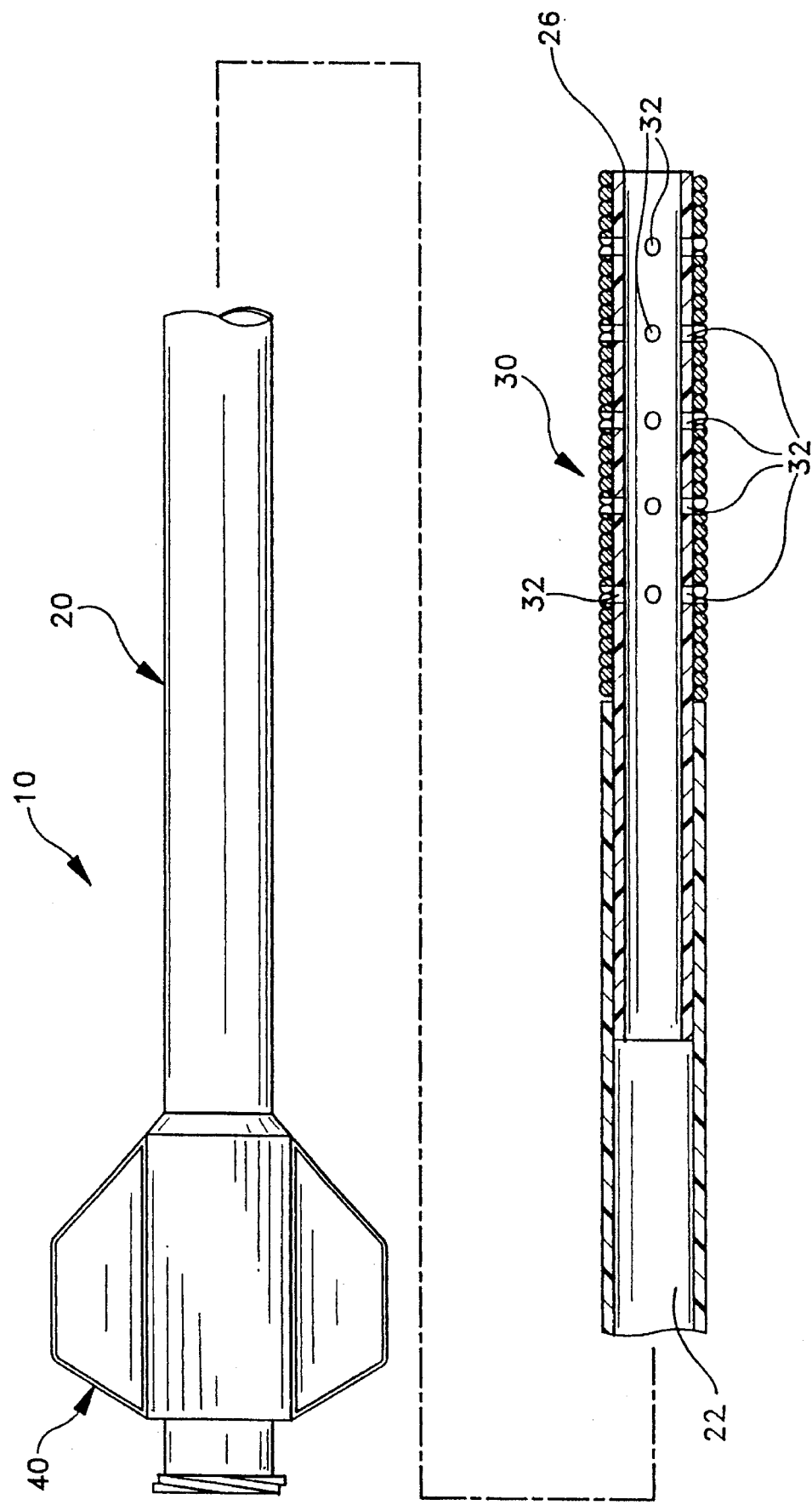
FIG. 1 is a side elevational view partially in section of one embodiment of the drug delivery device of this invention.

The drug delivery device 10 of this invention includes a hollow tube 20. In order to serve as a guide wire, tube 20 should have an outer diameter of from about 0.010 inches (0.0254 cm) to about 0.038 inches (0.097 cm), preferably from about 0.010 inches (0.0254 cm) to about 0.020 inches (0.051 cm), and more preferably about 0.014 inches (0.036 cm). Such outer diameters will allow device 20 to be inserted into very small blood vessels and allow it to cross very tight lesions. In addition, standard coronary guide wires have an outer diameter of 0.014 inches (0.036 cm). Thus, hollow tube 20 may serve as a guide wire for standard balloon dilatation catheters used in the coronary arteries. Of course, the desired outside diameter of the device will depend upon the particular application. Thus, a cerebral application will utilize generally smaller diameters (e.g., about 0.01 inches (0.0254 cm)), whereas applications in the upper leg will utilize generally larger diameters (e.g., about 0.035 inches (0.0889 cm)).

The wall thickness of tube 20 can generally vary between about 0.004 inches (0.01 cm) and about 0.00125 inches (0.0032 cm). The wall thickness should be large enough to maintain the structural integrity of tube 20 without unduly narrowing the lumen 22 of tube 20. Lumen 22 should remain large enough to allow drug formulations to be dispensed through openings 32 at a desired pressure and for a desired length of time. The diameter of lumen 22 will preferably be from about 0.010 inches (0.025 cm) to about 0.025 inches (0.064 cm).

In order for tube 20 to have lumen 22 extending therethrough yet have a sufficiently small outer diameter, it will preferably be formed from a shape-memory or superelastic material. Such a shape-memory or superelastic material is defined as an alloy that can be subjected to an apparent plastic deformation yet still return to its original shape when the load is released or when heated. This difference depends on the forming process of the shape-memory or superelastic material. It is to be understood that reference to a superelastic material hereinafter means a material having the above characteristics.

Suitable superelastic materials include nickel-titanium alloys (nitinol), nickel and its alloys or titanium and its alloys. Other examples of superelastic materials include, e.g., Silver-Cadmium (Ag-Cd), Gold-Cadmium (Au-Cd), Gold-Copper-Zinc (Au-Cu-Zn), Copper-Aluminum-Nickel (Cu-Al-Ni), Copper-Gold-Zinc (Cu-Au-Zn), Copper-Zinc (Cu-Zn), Copper-Zinc-aluminum (Cu-Zn-Al), Copper-Zinc-Tin (Cu-Zn-Sn), Copper-Zinc-Xenon (Cu-Zn-Xe), Iron Beryllium (Fe$_3$Be), Iron Platinum (Fe-Pt), Indium-Thallium (In-Tl), iron-manganese (Fe-Mn), Nickel-Titanium-Vanadium (Ni-Ti-V), Iron-Nickel-Titanium-Cobalt (Fe-Ni-Ti-Co) and Copper-Tin (Cu-Sn). See Schetsky, L. McDonald, "Shape Memory Alloys", *Encyclopedia of Chemical Technology* (3rd ed.), John Wiley & Sons, 1982, vol. 20. pp. 726–736 for a full discussion of superelastic alloys. One preferred nickel-titanium alloy can be obtained from Raychem Corporation of Menlo Park, Calif. under the trademark Tinel®. This material exhibits both flexibility and longitudinal stiffness. In addition, this material is tough, strong, biocompatible and bondable to the other components of device 10.

Alternative materials for the hollow tube include stainless steel and polymer-metal composites.

The distal portion of the device has a drug delivery portion 30 with at least one opening 32 for dispensing a drug formulation. Preferably from about 2 to about 40 openings 32 will be present. These holes may be on the sides of the distal portion of the tube as shown in FIG. 1, and, optionally, the distal tip 26 of tube 20 may also contain at least one opening 32 to allow a pharmaceutical solution to be dispensed therethrough. As shown in FIG. 6, distal tip 26 has a wall 21 with one or more openings 32'. In some cases, the distal tip 26 of tube 20 will contain at least one opening 32 and there will be no openings on the sides of the distal portion of the tube. The drug delivery portion will preferably be located in the distal-most segment of the tube, preferably within about 3 inches (7.6 cm) from the tip of the device, and more preferably within about 1.5 inches (3.8 cm) from the tip of the device.

Openings 32 may be perforations or slots of various shapes, such as ovals, circles, rectangles, or triangles with or without beveled edges. Methods of forming openings 32 are disclosed in Kraus et al. (U.S. Pat. No. 5,256,144); and Samson et al. (U.S. Pat. No. 4,998,923). Circular openings will generally have a diameter of about 0.01 inches (0.025 cm) to about 0.10 inches (0.25 cm).

In the embodiment shown in FIG. 7, distal segment 24 closes lumen 22 of tube 20. The solid wire has a proximal portion affixed to the distal end of tube 20. A helical coil is connected to the distal end of the solid wire. The solid wire of distal segment 24 is tapered in this configuration along its distal portion to increase its flexibility. Moreover, the solid wire may or may not extend to the distal end of the helical coil depending on the characteristics desired for distal segment 24. The solid wire and helical coil could be formed from stainless steel. Alternatively, the solid wire could be formed from a superelastic material and the helical coil could be formed from tungsten.

In yet another embodiment (not shown) the outer diameter of the solid wire of distal segment 24 is constant and is substantially equal to the inner diameter of the distal portion of tube 20. A small lumen is formed along a portion of the solid wire and in fluid communication with lumen 20 to provide a flow path to openings for drugs which are located in the solid wire. Again, the distal end of the solid wire in this embodiment may or may not be tapered and may or may not extend to the distal end of the helical coil.

The proximal end of device 10 may include a removable hub 40 to allow the attachment of other devices, such as an inflation/deflation device (not shown) to device 10. A standard Touhy Borst hub is preferable.

Device 10 can thus be used to perform a thrombolytic procedure. For example, a guide catheter can be maneuvered into position, and device 10 can be maneuvered through the guide catheter to the site of an occlusion. See FIG. 8. When openings 32 are properly aligned at about the site of the occlusion, drugs can be dispensed to perform a thrombolytic procedure. See FIG. 9.

After a thrombolytic procedure, a balloon may be needed to dilate a remaining thrombus or an underlying lesion. It may also be desirable to dilate a stenosis located in the proximity of the thrombotic obstruction. To perform a balloon dilatation procedure, the drug delivery portion 30 can first be moved distally past the (former) site of thrombotic obstruction. See FIG. 10. In some cases it will not be necessary or desirable to move the drug delivery portion 30 distally. In any event, hub 40 can then be removed and a wire guided balloon dilatation catheter 50 can be advanced over device 10 until the balloon 52 of that catheter is located at the desired site. The balloon 52 can then dilate the lesion or the obstruction. (See FIG. 11). Once the procedure is complete, both device 10 and the balloon dilatation catheter 50 can be removed. Balloon dilatation apparatuses and procedures are disclosed, e.g., in the following U.S. Pat. Nos. 5,306,247; 5,295,961; 5,232,445; 5,209,729; 5,163,906; 4,947,864; and 4,762,129. (All documents cited in this application, including the foregoing, are incorporated herein in their entireties for all purposes.)

Device 10 can also be used for other procedures, such as to deliver antiproliferatives to treat restenosis.

Device 10 can also be used as a guide wire to provide support for a stent deployment catheter. A wire guided stent delivery catheter can be advanced over device 10 until the stent is properly aligned at the treatment site. See FIG. 12. At this point the stent can be deployed in a conventional manner from the stent delivery catheter, leaving the stent in place. See FIG. 13. If desired, a balloon catheter can then be advanced over the device 10 until the balloon of that catheter is within the stent. The balloon can then be inflated to further expand the stent. The balloon can then be deflated and the balloon catheter removed. Stent deployment devices are disclosed, e.g., in U.S. Pat. No. 5,201,757.

Antithrombolytic, antithrombin, antiplatlet, antiproliferative, or any other type of drug, can be used with the present invention. The drug is typically introduced at the proximal end of the tube via a syringe. After the drug has been applied, generally at low pressures (e.g. from about 1.01 atmospheres to 4 atmospheres), and for the desired length of time (typically from about 20 seconds to about 3 minutes but in some cases for longer periods such as one day), injection is stopped. Specific examples of drugs that may be used with this invention are urokinase and heparin. Adjuncts may also be dispensed by the present invention, such as muscle relaxants, vasodilators, or any adjunct that may be used with invasive cardiology procedure. The drug formulations that will be used with the present invention will generally have viscosities from about 1 cp (centipoise) to about 19 cp. in small diameter devices, and about 1 cp to about 10,000 cp in larger diameter devices.

As used herein, the term drug formulation means any liquid, liquid based or gelitenacious drug or the like. The term includes, but is not limited to, liquid suspensions, liquid emulsions, gels, suspensions, colloidal suspensions, liquid mixtures, liquid/solid mixtures, thixotropic solutions, and the like.

When dispensing drug formulations, at least one opening 32 will generally be aligned at the occlusion. Preferably, all or most of the openings 32 will be adjacent to the blockage to conserve the amount of drugs that are used. However, the present invention will generally be effective even when some or all of the openings are somewhat upstream or downstream from the occlusion at the time that the drug formulations are infused.

Although this invention has been described in connection with performing thrombolytic procedures, angioplasty, and stent deployment procedures on coronary arteries, it is to be understood that the invention has equal applicability to angioplasty and stent deployment procedures performed in other peripheral arteries such as the carotid artery, the cerebral arteries, and the renal artery. The present invention can readily be built to be compatible with 0.021 inch to 0.035 inch (0.053 cm to 0.089 cm) and/or 0.038 inch (0.097 cm) systems which are typically used in the periphery. The present invention can also be used in different intraluminal procedures, such as in the removal of stenoses using laser light energy as disclosed in U.S. Pat. No. 5,176,674.

Thus it is seen that a drug delivery device is provided that can cross a very tight occlusion or an extremely narrow blood vessel. One skilled in the art will appreciate that the described embodiments are presented for purposes of illustration and not of limitation.

We claim:

1. A drug delivery device comprising:

a hollow tube including means sized and configured to serve as a guidewire for intraluminal devices and having a proximal portion and a distal portion and defining a lumen therein;

the distal portion of the tube having at least one opening having a diameter suitable for the infusion of a drug formulation therethrough, the opening being in fluid communication with the lumen.

2. The drug delivery device of claim 1 wherein the hollow tube is formed from a superelastic material.

3. The drug delivery device of claim 2 wherein the superelastic material is selected from the group consisting of a nickel-titanium alloy, nickel and its alloys, and titanium and its alloys.

4. The drug delivery device of claim 2 wherein the tube has an outer diameter of from about 0.010 inches (0.025 cm) to about 0.038 inches (0.097 cm).

5. The drug delivery device of claim 4 wherein the tube has an outer diameter of about 0.014 inches (0.036 cm).

6. The drug delivery device of claim 4 wherein the lumen has a diameter of from about 0.005 inches (0.013 cm) to about 0.035 inches (0.089 cm).

7. The drug delivery device of claim 1 further comprising a flexible distal segment connected to the distal portion of the hollow tube.

8. The drug delivery device of claim 7 wherein the flexible distal segment comprises a generally solid core wire.

9. The drug delivery device of claim 8 further comprising a helical coil spring arranged coaxially about the generally solid core wire.

10. A drug delivery-dilatation device, comprising:

a hollow tube including means configured to serve as a guidewire for intraluminal devices and having a proximal portion and a distal portion and defining a lumen therein, the distal portion of the tube having at least one opening having a diameter suitable for the infusion of a drug formulation therethrough, the opening being in fluid communication with the lumen; and a balloon dilatation catheter comprising a dilatation balloon attached to a catheter, the catheter having a guide wire lumen adapted to receive the hollow tube.

11. The drug delivery-dilatation device of claim 10 wherein the hollow tube is formed from a superelastic material.

12. The drug delivery-dilatation device of claim 11 wherein the superelastic material is selected from the group consisting of a nickel-titanium alloy, nickel and its alloys, and titanium and its alloys.

13. The drug delivery-dilatation device of claim 11 wherein the tube has an outer diameter of from about 0.010 inches (0.025 cm) to about 0.038 inches (0.097 cm).

14. The drug delivery-dilatation device of claim 13 wherein the tube has an outer diameter of about 0.014 inches (0.036 cm).

15. The drug delivery-dilatation device of claim 13 wherein the lumen has a diameter of from about 0.005 inches (0.013 cm) to about 0.035 inches (0.089 cm).

16. The drug delivery-dilatation device of claim 10 wherein the catheter guide wire lumen is at least partially disposed about the hollow tube.

17. A drug delivery-stent deployment device, comprising:

a hollow tube including means configured to serve as a guidewire for intraluminal devices and having a proximal portion and a distal portion and defining a lumen therein, the distal portion of the tube having at least one opening having a diameter suitable for the infusion of a drug formulation therethrough, the opening being in fluid communication with the lumen; and a stent deployment catheter having a guide wire lumen adapted to receive the hollow tube.

18. The drug delivery-stent deployment device of claim 17 wherein the hollow tube is formed from a superelastic material.

19. The drug delivery-stent deployment device of claim 18 wherein the superelastic material is selected from the group consisting of a nickel-titanium alloy, nickel and its alloys, and titanium and its alloys.

20. The drug delivery-stent deployment device of claim 18 wherein the tube has an outer diameter of from about 0.010 inches (0.025 cm) to about 0.038 inches (0.097 cm).

21. The drug delivery-stent deployment device of claim 20 wherein the tube has an outer diameter of about 0.014 inches (0.036 cm).

22. The drug delivery-stent deployment device of claim 20 wherein the lumen has a diameter of from about 0.005 inches (0.013 cm) to about 0.035 inches (0.089 cm).

23. The drug delivery-stent deployment device of claim 17 wherein the catheter guide wire lumen is at least partially disposed about the hollow tube.

24. A method for removing a thrombotic blockage using a drug delivery device with a hollow tube having a proximal portion and a distal portion and defining a lumen therein, wherein the distal portion has a drug delivery portion having at least one opening having a diameter suitable for the infusion of a thrombolytic agent therethrough, the opening being in fluid communication with the lumen, the method comprising:

advancing the drug delivery device through a patient's vasculature so that the drug delivery portion is located at about a site of thrombotic obstruction; and infusing the thrombolytic agent through the opening to reduce the thrombotic obstruction.

25. The method of claim 24, wherein an underlying lesion is revealed after the thrombolytic agents are infused, the method further comprising:

advancing a balloon dilatation catheter over at least part of the hollow tube so that a dilatation balloon is located adjacent to the underlying lesion; and dilatating the underlying lesion with the dilatation balloon.

26. The method of claim 24 further comprising:

advancing a stent delivery catheter with a stent contained therein over at least part of the hollow tube; and deploying the stent from the stent delivery catheter.

27. The method of claim 26, further comprising:

withdrawing the stent delivery catheter;

advancing a balloon catheter over at least part of the hollow tube until a balloon is located within the stent; and inflating the balloon to expand the stent.

28. The drug delivery device of claim 24 wherein the tube has an outer diameter of from about 0.010 inches (0.025 cm) to about 0.038 inches (0.097 cm).

29. The drug delivery device of claim 28 wherein the tube has an outer diameter of about 0.014 inches (0.036 cm).

30. The drug delivery device of claim 28 wherein the lumen has a diameter of from about 0.005 inches (0.013 cm) to about 0.035 inches (0.089 cm).

31. The drug delivery device of claim 1 wherein the distal portion of the tube has a distal tip and at least one opening is proximal the distal tip.

32. The drug delivery device of claim 10 wherein the distal portion of the tube has a distal tip and at least one opening is proximal the distal tip.

33. The drug delivery device of claim 17 wherein the distal portion of the tube has a distal tip and at least one opening is proximal the distal tip.

34. The drug delivery device of claim 24 wherein the distal portion of the tube has a distal tip and at least one opening is proximal the distal tip.

\* \* \* \* \*